United States Patent [19]

Schaeffer

[11] 4,233,263
[45] Nov. 11, 1980

[54] METHOD OF MAINTAINING BACTERIAL STERILITY IN URINE DRAINAGE BAGS

[75] Inventor: Anthony J. Schaeffer, Western Springs, Ill.

[73] Assignee: Northwestern University, Evanston, Ill.

[21] Appl. No.: 25,753

[22] Filed: Apr. 2, 1979

[51] Int. Cl.³ .................... A01N 59/00; A61B 19/00; A61L 2/18; A61M 27/00
[52] U.S. Cl. .................... 422/28; 128/350 R; 128/DIG. 24
[58] Field of Search ............ 422/28; 128/DIG. 24, 128/350 R, 350 V

[56] References Cited

U.S. PATENT DOCUMENTS

| 3,417,750 | 12/1968 | Carson | 128/350 V |
| 3,848,603 | 11/1974 | Throner | 128/350 V |
| 3,905,368 | 9/1975 | Lewis et al. | 128/DIG. 24 |

FOREIGN PATENT DOCUMENTS 2434270  2/1976  Fed. Rep. of Germany ............ 422/28

*Primary Examiner*—Bradley R. Garris
*Attorney, Agent, or Firm*—Tilton, Fallon, Lungmus & Chestnut

[57] ABSTRACT

Urine drainage bags connected to indwelling catheters are maintained in bacterially sterile condition by periodic addition of small quantities of 3% U.S.P. hydrogen peroxide solution. The method protects both the bladder and the hospital environment from bacterial contamination.

7 Claims, No Drawings

METHOD OF MAINTAINING BACTERIAL STERILITY IN URINE DRAINAGE BAGS

BACKGROUND AND PRIOR ART

The catheterized urinary tract is the most common site of hospital-acquired infection and accounts for approximately 30 percent of all nosocomial infections. A significant improvement in the prevention of catheter-associated bacteriuria has been the conversion from "open" to "closed sterile" drainage systems. Nevertheless, over 20 percent of patients with indwelling catheters continue to acquire urinary infections. See Garibaldi et al, New England J. Med., 291:215–219 (1974). Previous studies have suggested that prevention of bacterial contamination of the drainage system by addition of oxycyanide (Dukes, Proc. Roy. Soc. Med. 22:259–269, 1928), formalin (Roberts, et al, Brit. J. Urol. 37:63–72, 1965), or chlorhexidine (Webb et al, Brit, J. Urol. 40(3):585–588, 1968) delayed the onset of bacteriuria. However, these agents are either toxic or not available in the United States.

While it is desirable to reduce the incidence of catheter-associated bacteriuria, such urinary tract infections cannot be eliminated. Therefore, a serious problem in the management of catheterized patients in the hospital environment is that of cross-contamination. The urine collection bags must be emptied at frequent intervals, usually at least once every eight hours, and the removal of bacterially-contaminated urine can lead to the spread of infection. A patient in the same room with a catheterized patient has an increased risk of acquiring an infection. The risk of spreading infection is even greater when the other patient in the room is also catheterized. Even patients in adjoining rooms have a significantly higher risk of infection. In order to minimize cross-contamination, the collected urine must be maintained in sterile condition during the period of collection even when the urine has a high bacterial count when it enters the drainage bag.

SUMMARY OF INVENTION

The present invention is based on the discovery that the problems referred to above can be substantially alleviated by the use of a readily available hospital antiseptic; namely, 3% U.S.P. hydrogen peroxide solution. In practicing the method of this invention, a small amount (e.g. 30 ml) of the hydrogen peroxide solution is introduced into the urinary drainage bag prior to each period of urine collection. Surprisingly, even if the urine is highly contaminated with bacteria, essentially sterile conditions are thereby maintained in the collection bag as the urine continues to be voided for periods of several hours (viz. 8 hours). This effect was not predictable on the basis of prior knowledge, since dilute solutions of hydrogen peroxide are known to be unstable in the presence of bacteria and organic substances. For the purpose of the present invention, it is important that the urine be in sterile condition throughout the collection period, thereby protecting the patient from infection via the bag during collection, and the hospital environment and nearby patients from contamination on emptying the bag. The present invention accomplishes these results in a simple and efficient manner which permits its immediate adoption in hospitals. Furthermore, the urinary drainage system can be modified to provide even greater convenience of use by incorporating special means for the periodic introduction of the hydrogen peroxide solution.

DETAILED DESCRIPTION

The method of the present invention is adapted for use with sterile closed urinary drainage systems, such as catheter drainage systems or urostomy bags. Such systems and bags are manufactured and sold, respectively, by Travenol Laboratories, Inc., Deerfield, Ill., and Hollister, Inc., Chicago, Ill., and other U.S. manufacturers. A catheter system will include a urinary catheter of the indwelling-type. The external end of the catheter is connected to a drainage tube, which connects to a urine drainage bag for collection of the discharged urine. The bags are in the form of flexible plastic pouches, and usually have a maximum capacity of approximately two liters. Means are provided for supporting the bag, such as the cord-type hanger with the bag extending downwardly from the support. The top of the bag is provided with an inlet fitting to which the drainage tube is connected, and the bottom of the bag is provided with a discharge fitting to which a discharge tube is connected. Means are provided for releasably clamping the discharge tube, such as a cut-off clamp. There may also be provided a fastener device for holding the drainage tube against the bag when in closed condition. The present invention does not involve or require any specific design of the urinary drainage system. In general, the method of this invention for maintaining bacterial sterility can be applied to any urine drainage bag in a closed urinary drainage system, including urostomy bags which have an upper inlet applied over the ostomy and a bottom outlet with openable clamp or spigot.

In hospitals, 3% U.S.P. hydrogen peroxide solution is readily available. According to the United States Pharmacopeia definition, 3% hydrogen peroxide solution is a solution of hydrogen peroxide in water containing not less than 2.5 grams and not more than 3.5 grams of $H_2O_2$ in each 100 milliliters of solution. In other words, as thus defined, and for the purpose of the present invention, the solution will contain from 0.025 to 0.035 grams of $H_2O_2$ per milliliter.

In hospital practice, urine collection bags are emptied periodically, usually at least every six to ten hours. The average is about once every eight hours, which corresponds with the eight-hour duration nursing shifts that are standard practice. Therefore, urine collection bags will normally be emptied once during each nursing shift, that is, three times in each twenty-four hour period at intervals of about eight hours. The amount of urine collected will vary with the patient, but averages about 500 ml per eight hours. The range is from about 200 to 1,000 ml/8 hrs., but urine collections at the low and high ends of this range are unusual. However, the method of the present invention is adapted for use over the range of normal urine volume collection in hospitals, and it is unnecessary to adjust the amount of hydrogen peroxide solution used due to variation in the volume of the urine from a particular patient.

The essential step in the method consists of introducing into the urine drainage bag before each period of urine collection from 15 to 60 milliliters of 3% hydrogen peroxide. For example, this may be accomplished by using a sterile syringe, and introducing the hydrogen peroxide solution through the discharge tube immediately after emptying the bag. After the hydrogen peroxide solution has been added to the bag, the drainage tube is closed in the usual way, and a new period of urine collection is started. Bacterially-contaminated urine is thereby sterilized as it enters the bag not only for the first portion of the urine collection, but continuously throughout the urine collection. As will subsequently be described in greater detail, experimental evidence has shown that essentially sterile urine is maintained for collection periods up to eight hours. In a preferred procedure, from 20 to 40 ml of 3% $H_2O_2$ solution are introduced into the bags each time the urine is emptied, and, preferably also when the drainage system is first applied to the patient. However, when the patient is known to be free of urinary tract infection at the time of catheterization, the use of the hydrogen peroxide solution can be deferred until the first emptying of the bag, or at a subsequent time, if the urine is found to be infected. As a precaution, however, it is desirable to apply the method as completely and continuously as possible.

The method of this invention and the results obtained thereby are further illustrated by the following examples.

EXPERIMENTAL EXAMPLES

An experimental study was carried out at the 20-bed spinal cord injury unit of Northwestern Memorial Hospital, Chicago, Ill., from May 1977 to December 1978. The study population consisted of consecutive patients with acute spinal cord injury who required continuous indwelling urethral catheter drainage and received no antimicrobial therapy. The methods and results were as follows:

Latex catheters (16 or 18 F.), bottom vented primary drainage bags without anti-reflux devices and two liter sterile secondary bags were used, as commercially available from Travenol Laboratories, Inc., Deerfield, Ill. The urinary bags contained self-sealing rubber ports near the catheter-tubing junction and in the drainage spigot for aseptic aspiration of urine.

Indwelling catheters were inserted by nursing personnel after cleansing the urethra with benzalkonium chloride. Patients were randomized to one of three systems of urine drainage, (1) Control: Conventional closed sterile drainage. (2) Saline: Conventional drainage to which a sterile secondary bag was attached for instillation of saline into the primary bag and collection of urine, (3) Hydrogen peroxide: Conventional drainage to which a secondary bag was attached for instillation of hydrogen peroxide into the primary bag and collection of urine.

Control patients were managed with conventional techniques of closed sterile urinary drainage. Urine was collected every eight hours into clean receptacles. In the modified drainage groups, the secondary bag which contained either 30 ml of sodium chloride injection, U.S.P., or 30 ml 3% hydrogen peroxide was attached aseptically to the primary drainage spigot. The contents were transferred from the secondary bag to the primary bag and the tubing clamped. Eight hours later, the tubing was unclamped and the urine drained into the secondary bag. The secondary bag was removed, a new secondary bag attached and the cycle repeated. The urethral meatus was washed every morning with water and bladder irrigation was avoided.

Specimens were collected at the time of catheter insertion and daily thereafter by a member of the study team. Urethral cultures were performed by retracting the urethra approximately 1 cm and circmferentially sampling the secretions of the exposed catheter with a dry sterile cotton swab. The swab was placed in 4.5 ml of Stuart's transport medium, agitated in a laboratory mixer and the swab discarded. Urine was obtained by aseptic needle puncture from the catheter-tubing junction and the drainage spigot ports just prior to emptying the primary bag. Specimens were refrigerated within one hour and 0.1 m. streaked on blood and MacConkey's agar plates. Standard bacteriologic methods were used to quantitate and identify all organisms. Selected strains were serotyped. Patients who had ten or more organisms per milliliter in either of the initial urine specimens were considered to have bacteriuria and were eliminated from the study. In subsequent cultures, colony counts of $10^2$ organisms per milliliter or more were judged to indicate bacterial colonization of bladder urine. Any number of organisms isolated from urethral specimens were considered significant.

Observations of the patients' clinical status and the quality of the nursing and catheter care were made daily. Patients were followed until discharged, or the catheter was removed, or the bladder urine contained more than $10^5$ colonies per milliliter on at least two consecutive days, or antimicrobials were administered.

The 31 patients studied were abacteriuric (less than 10 colonies per milliliter) at the time of and 24 hours after catheterization, received no antimicrobial agents, and remained catheterized for more than 24 hours. None had a significant urologic or medical history except for one man who required insulin for adult onset diabetes mellitus. Only one patient was uncircumsized.

Of the 31 patients studied, 26 (84 percent) acquired bladder bacteriuria (catheter-culture end point) with at least $10^4$ colonies per milliliter and 23 (74 percent) and greater than $10^5$ colonies per milliliter. Nine (35 percent) of 26 patients had initial bladder bacteriuria less than $10^4$ colonies per milliliter for one to two days (means 1.1 days) prior to developing at least $10^4$ colonies per milliliter. In ten instances (9 patients) however, transient bladder bacteriuria lasting 1 to 2 days (mean 1.3) occurred which did not reach $10^4$ colonies per milliliter. Eleven of 12 patients with conventional drainage and 6 of 9 with hydrogen peroxide modified drainage acquired bacteriuria with at least $10^4$ organisms per milliliter.

Bacterial contamination of the urinary drainage bag was observed prior to bladder bacteriuria in 32 and 20 percent of the specimens obtained from the control and saline systems respectively. Of the 12 patients with positive bag cultures, seven (58 percent) acquired bladder bacteriuria from this source. Colony counts in the bag urine were usually greater than $10^4$ organisms per milliliter and persisted for a mean of 1.2 days prior to development of bladder bacteriuria. All of the bag urine cultures from the hydrogen peroxide system showed no growth ($p<0.01$). The data is summarized in Table A. The bacteria which were isolated from the drainage bag urine prior to colonizing the bladder included: E. coli, S. marcesens, and S. epidermidis. In addition, E. coli, C. freundii, E. agglomerans, Pseudomonas species, and coryneforms were recovered from bag urine but did not colonize the bladder from this source.

After bladder bacteriuria developed, all of the 51 drainage bag cultures obtained from the control and saline groups were positive whereas only 5 percent of the cultures from the hydrogen peroxide drainage system showed growth (400 and 600 colonies per milliliter) ($p<0.0005$). In both instances, subsequent bag cultures showed no growth. The data is summarized in Table B.

The possibility that catheter-associated urinary infections can be due to organisms transmitted between patients by cross-contamination was suggested in two instances involving conventional drainage systems. In one patient, Pseudomonas (greater than $10^5$ colonies per milliliter) was isolated from bladder and bag urine cultures within 48 hours of shared room exposure to another catheterized patient with Pseudomonas bacteriuria. Another episode involved an individual who shared a room with a patient with a catheter-associated *E. coli* (06) urinary infection. On the fifth day of exposure, *E. coli* (06) (600 colonies per milliliter) was isolated from the bag urine culture and the following day *E. coli* (06) (greater than $10^5$ colonies per milliliter) was identified in both the bladder and bag specimens. Error in the care of the closed drainage system was not observed in either case, but in each, the same nursing personnel and hand washing facilities were involved.

The cumulative probability of bacteriuria free survival for each group was determined, using the method of Peto et al, British J. Cancer 35:1-39, 1977. The median survival was 4.5,5 and seven days for the control saline and hydrogen peroxide groups respectively. The longest period that a patient in the control, saline, and hydrogen peroxide groups was abacteriuric was 6, 12 and 16 days respectively. The difference in the cumulative probability of bacteriuria free survival between the control and hydrogen peroxide drainage groups was significant ($p<0.05$). This data indicates that bacterial contamination of the drainage bag is a frequent source of bladder bacteriuria which can be effectively eliminated by periodic instillation of hydrogen peroxide.

Summarizing, the study shows that the addition of a small quantity (30 ml) of 3% $H_2O_2$ to the drainage bag after emptying the collected urine protects both the bladder and the hospital environment from bacterial contamination for intervals of at least 8 hours.

UROSTOMY EXAMPLE

The same procedure described above is followed with patients using urostomy bags. Following emptying of the collected urine, 30 ml of 3% $H_2O_2$ is added to the bag through the outlet before it is closed and the next collection period commenced.

TABLE A

Relation Between Catheter Drainage System and Frequency of Bag Bacteriuria in Patients without Bladder Bacteriuria[1]

| Drainage System | Bag Urine Cultures No. | No. $\geq 10^2$ colonies/ml | P value VS. $H_2O_2$ |
|---|---|---|---|
| Control | 34 | 11 (32%) | <0.001 |
| Saline | 46 | 9 (20%) | <0.01 |
| Hydrogen Peroxide | 44 | 0 (0%) | |

[1] <10 colonies/ml

TABLE B

Relation Between Catheter Drainage System and Frequency of Bag Bacteriuria in Patients with Bladder Bacteriuria[1]

| Drainage System | Bag Urine Cultures No. | No. $\geq 10^2$ colonies/ml | P value vs. $H_2O_2$ |
|---|---|---|---|
| Control | 24 | 24 (100%) | <0.0005 |
| Saline | 27 | 27 (100%) | <0.0005 |
| Hydrogen Peroxide | 38 | 2 (5%)[2] | |

[1] $\geq 10^4$ colonies/ml
[2] Subsequent bag cultures showed no growth, suggesting that through procedural omission the hydrogen peroxide solution had not been added to the bags after emptying when growth was observed in the next urine collection.

I claim:

1. The method of maintaining bacterial sterility in a urine drainage bag of a closed urinary drainage system, wherein urine is collected in said bag for several hours and then emptied therefrom, consisting essentially of introducing into said bag before each period of urine collection from 15 to 60 milliliters of an aqueous solution of hydrogen peroxide ($H_2O_2$) containing from 0.025 to 0.035 grams of $H_2O_2$ per milliliter.

2. The method of claim 1 in which from 20 to 40 milliliters of said $H_2O_2$ solution are introduced.

3. The method of maintaining bacterial sterility in a urine drainage bag in a closed urinary drainage system, wherein urine is collected in said bag for a period of from 6 to 10 hours and then emptied therefrom, consisting essentially of introducing into said bag before each period of urine collection from 20 to 40 milliliters of 3% hydrogen peroxide (U.S.P.).

4. The method of claim 3 in which approximately 30 milliliters of said $H_2O_2$ solution are introduced.

5. The method of maintaining bacterial sterility in a urine drainage bag connected to an indwelling catheter in a closed drainage system, wherein urine is collected in said bag for periods of from 6 to 10 hours and then emptied therefrom, consisting essentially of introducing into said bag before each period of urine collection from 15 to 60 milliliters of an aqueous solution of hydrogen peroxide ($H_2O_2$) containing from 0.025 to 0.035 grams of $H_2O_2$ per milliliter.

6. The method of claim 5 in which from 20 to 40 milliliters of said $H_2O_2$ solution are introduced.

7. The method of maintaining bacterial sterility in a urine drainage bag connected to an indwelling catheter in a closed urinary drainage system, wherein urine is collected in said bags for a period of approximately 8 hours and then emptied therefrom, consisting essentially of introducing into said bag before each period of urine collection approximately 30 milliliters of 3% hydrogen peroxide (U.S.P.).

* * * * *